US008097420B1

(12) United States Patent
Doyle et al.

(10) Patent No.: US 8,097,420 B1
(45) Date of Patent: Jan. 17, 2012

(54) METHOD OF DIAGNOSIS

(75) Inventors: Ian Ross Doyle, Marino (AU); Andrew David Bersten, Seacliff (AU); Terence Evan Nicholas, Eastwood (AU)

(73) Assignee: Southern Medical Diagnostics Pty Ltd, North Adelaide (AU)

( * ) Notice: Subject to any disclaimer, the term of this patent is extended or adjusted under 35 U.S.C. 154(b) by 0 days.

(21) Appl. No.: 09/486,703

(22) PCT Filed: Sep. 4, 1998

(86) PCT No.: PCT/AU98/00723
§ 371 (c)(1),
(2), (4) Date: Jun. 27, 2000

(87) PCT Pub. No.: WO99/13337
PCT Pub. Date: Mar. 18, 1999

(30) Foreign Application Priority Data

Sep. 5, 1997 (AU) ...................................... PO8999
Aug. 4, 1998 (AU) ...................................... PP5062

(51) Int. Cl.
*G01N 33/53* (2006.01)
(52) U.S. Cl. ........................................ 435/7.1; 436/811
(58) Field of Classification Search .................... 435/7.1, 435/7.9, 7.92, 7.93, 7.94, 7.95; 436/518, 436/63, 811
See application file for complete search history.

(56) References Cited

U.S. PATENT DOCUMENTS

| 5,156,950 | A | 10/1992 | Akino et al. |
| 5,573,920 | A | 11/1996 | Randle |
| 5,670,328 | A | 9/1997 | Inoue et al. |
| 2004/0121343 | A1 | 6/2004 | Buechler et al. |

FOREIGN PATENT DOCUMENTS

| EP | 0 224 590 | 6/1987 |
| EP | 0 329 794 | 8/1989 |
| EP | 0 511 011 | 10/1992 |
| EP | 0 602 248 | 6/1994 |
| JP | 04-009665 | 1/1992 |
| JP | 6-506827 | 8/1994 |
| WO | 93/25701 | 12/1993 |
| WO | WO 93/25701 | 12/1993 |
| WO | WO 00/05585 | 2/2000 |

OTHER PUBLICATIONS

Stedman's Medical Distionary 27th Edition, definition of asymptomatic, 2007.*
Stedman's Medical Dictionary 27th Edition, definition of normal, 2007.*
Online Medical Dictionary, definition of asymptomatic, 2007.*
Stedman's medical dictionary 24th edition, 1988, p. 960.*
Holmes in Manual of Clinical Laboratory Immunology, 1997, p. 1158, col. 1, second full paragraph.*

Ian R. Doyle et al., "Distribution of Surfactant Protein A in Rat Lung.", American Journal of Respiratory Cell and Molecular Biology vol. 2, pp. 405-415, 1994.
Ian R. Doyle et al., "Serum Surfactant Protein-A Levels in Patients with Acute Cardiogenic Pulmonary Edema and Adult Respiratory Distress Syndrome.", American Journal of Respiratory Critical Care Medicine, vol. 152, pp. 307-317, 1995.
Gouri Yogalingam et al., "Expression and distribution of surfactant proteins and lysozyme after prolonged hyperpnea.", American Journal of Physiology, vol. 14, pp. L320-L330, 1996.
Ian R. Doyle et al., "Differential changes in SP-A and disaturated phospholipids in the isolated perfused rat lung and in vivo.", American Journal of Physiology, pp. L374-L382, 1996.
Ian R. Doyle et al., "Quantity and Structure of Surfactant Proteins Vary Among Patients with Alveolar Proteinosis.", American Journal of Respiratory Critical Care Medicine, vol. 157, pp. 658-664, 1998.
A. D. Bersten et al., "Surfactant composition reflects lug overinflation and arterial oxygenation in patients with acute lung injury.", European Respiratory Journal, vol. 12, pp. 301-308, 1998.
Ian R. Doyle et al., "Clearance of Clara Cell Secretory Protein 16 (CC16) and Surfactant Proteins A and B from Blood in Acute Respiratory Failure.", American Journal of Respiratory Critical Care Medicine, vol. 158, pp. 1528-1535, 1998.
B. A. Dilena et al., "Six alternative methods to the lecithin/sphingomyelin ratio in amniotic fluid for assessing fetal lung maturity.", Annual Clinical Biochemistry, vol. 34, pp. 106-108, 1997.
Terence E. Nicholas et al., "Surfactant replacement therapy in ARDS: white knight or noise in the system?", Thorax, vol. 52, pp. 195-197, 1997.
A. D. Bersten, "Respiratory Mechanics and Surfactant in The Acute Respiratory Distress Syndrome.", Clinical and Experimental Pharmacology and Physiology, vol. 25, pp. 955-963, 1998.
A. D. Bersten, "Respiratory Mechanics and Surfactant in The Acute Respiratory Distress Syndrome.", Proceedings of the Australian Physiological and Pharmacological Society, vol. 29, No. 1, pp. 50-65, 1998.
Ian R. Doyle et al., "Leakage of Surfactant Proteins in Acute Respiratory Distress Syndrome.", Proceedings of the Australian Physiological and Pharmacological Society, vol. 29, No. 1, pp. 66-89, 1998.
Ian R. Doyle et al., "Partitioning Lung and Plasma Proteins: Circulating Surfactant Proteins as Biomarkers of Alveolocapillary Permeability.", Clinical and Experimental Pharmacology and Physiology, vol. 26, pp. 185-197, 1999.
J. H. T. Power et al., "Ultrastructural and Protein Analysis of Surfactant in the Australian Lungfish. *Neoceratodus forsteri*: Evidence for Conservation of Composition of 300 Million Years.", the Journal of Experimental Biology, vol. 202, pp. 2543-2550, 1999.

(Continued)

*Primary Examiner* — Patricia A Duffy
(74) *Attorney, Agent, or Firm* — Kenyon & Kenyon LLP

(57) ABSTRACT

The present invention relates generally to a method of diagnosing or predicting the development of lung damage and more particularly, to a method of diagnosing or predicting the development of alveolo-capillary membrane damage. The method of the present invention is useful inter alia for detecting lung damage or predicting the development of lung damage such as that caused by noxious agents or as an undesirable side effect resulting from exposure to a therapeutic agent and for monitoring the progress of lung damage.

15 Claims, 1 Drawing Sheet

OTHER PUBLICATIONS

Figure 1:
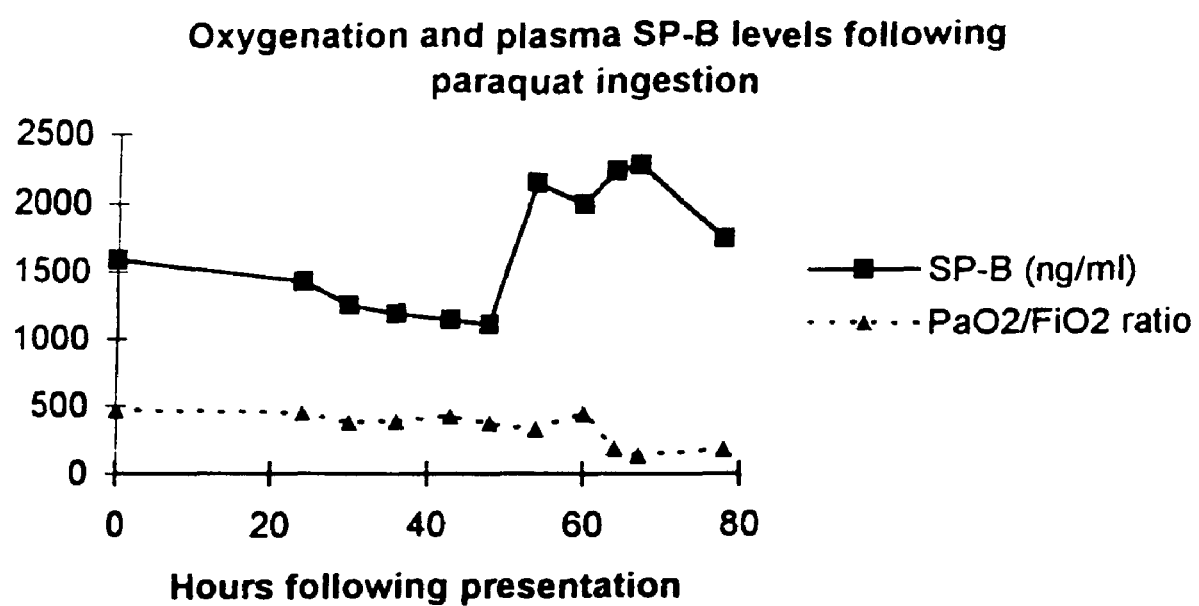

Series of Abstracts from conference proceedings: A587, A11, A639, A723, A644, A105, A211, A90, A392, A682, A347, A379, A600, A705 and Abstract for Paediatric Society of Australia and New Zealand, 1999, p. 38 (of 41).

Ian R. Doyle et al., "Composition of Human Pulmonary Surfactant Varies with Exercise and Level of Fitness.", American Journal of Respiratory Critical Care Medicine, vol. 149, pp. 1619-1627, 1994.

Ian R. Doyle et al., "Surfactanat as a Marker of Disease Severity in Critically III Patients with Respiratory Failure.", Advances in Critical Care Testing, Eds. List, Muller and McQueen. (6 pages), Jan. 1997.

Rubin P. et al., "Surfactant Release as an Early Measure of Radiation Pneumonitis", *International Journal of Radiation Oncology, Biology, Physics*, 9(11), pp. 1669-1674 (1983).

Lewis J. et al., "Altered Alveolar Surfactant is an Early Marker of Acute Lung Injury in Septic Adult Sheep", *American Journal of Respiratory and Critical Care Medicine*, 150(1), pp. 123-130 (1994).

Robertson et al., "Alveolar-To-Vascular Leakage of Surfactant Protein A in Ventilated Immature Newborn Rabbits", *Biology of the Neonate*, 68(3), pp. 185-190 (1995).

Lachmann, B., "The Role of Lung Surfactant in ARDS", *European Journal of Respiratory Diseases*, 62, pp. 13-14 (1983).

Doyle et al., "Surfactant Proteins (SP-A and B) in Plasma in Criticaly III Patients Respiratory Disease", *American Journal Respiratory Critical Care Medicine*, 151:A73 (1995), (Abstract Only).

Doyle et al., "Surfactant Protein A (SP-A) in Serum as a Marker for Lung Injury in Patients With Adult Respiratory Distress Syndrome (ARDS)", *American Journal Respiratory Critical Care Medicine*, 149:A567 (1994), (Abstract Only).

Lewis J. et al., "Surfactant and the Adult Respiration Distress Syndrome", *American Review of Respiratory Disease*,147(1), pp. 218-233 (1993).

M. Guazzi "Alveolar-capillary membrane dysfunction in chronic heart failure: pathophysiology and therapeutic implications," *Clinical Science* 98:633-641, 2000.

Kaplan et al. "A positron emission tomographic comparison of pulmonary vascular permeability during the adult respiratory distress syndrome and pneumonia," *American Review of Respiratoty Disease* 143:150-154, 1991.

Townsley et al. "Pulmonary microvascular permeability: Responses to high vascular pressure after induction of pacing-induced heart failure in dogs" *Circulation Research* 77:317-325, 1995.

Huang et al. "Capillary filtration is reduced in lungs adapted to chronic heart failure: morphological and haemodynamic correlates," *Cardiovascular Research* 49:207-217, 2001.

S. Shimura et al., "Surfactant aproprotein-A concentration in airway secretions for the detection of pulmonary oedema," *Eur Respir J.*, 9, pp. 2525-2530, 1996.

De Pasquale et al., "Infarct-induced chronic heart failure increases bidirectional protein movement across the alveolocapillary barrier," *Am J Physiol Heart Circ Physiol.*, 284, pp. H2136-H2145, Feb. 6, 2003.

Bersten et al., "Elevated plasma surfactant protein-B predicts development of acute respiratory distress syndrome in patients with acute respiratory failure," *Am J Respir Crit Care Med.*, 164, pp. 648-652, 2001.

Kuroki et al., "Elevated levels of lung surfactant protein A in sera from patients with idiopathic pulmonary fibrosis and pulmonary alveolar proteinosis,"*Am Review of Respir Disease*,147, pp. 723-729, 1993.

International Search Report, PCT Application No. PCT/AU2004/000252, dated May 4, 2004.

Hankinson et al., "Spirometric reference values from a sample of the general U.S. population," *Am J Respir Crit Care Med*, 159, pp. 179-187, 1999.

Translation of Office Action, Japanese Application No. 2000-511069, dated Mar. 31, 2009.

Jennings et al., "Pulmonary alveolar proteinosis in SCID mice," *Am J Respir Cell Mol Biol.*, 13, pp. 297-306, 1995.

Nogee et al., "Increased expression of pulmonary surfactant proteins in oxygen-exposed rats," *Am J Respir Cell Mol Biol.*, 4, pp. 102-107, 1991.

Chida et al., "Surfactant proteins and anti-surfactant antibodies in sera from infants with respiratory distress syndrome with and with surfactant treatment," *Pediatrics*, 88, 1, pp. 84-89, 1991.

Honda et al.; "Pulmonary Surfactant Protein D in Sera and Bronchoalveolar Lavage Fluids"; Am J. Respir. Crit. Care Med.; vol. 152; 1995; pp. 1860-1866.

Honda et al.; "Aberrant Appearance of Lung Surfactant Protein A in Sera of Patients with Idiopathic Pulmonary Fibrosis and its Clinical Significance"; Respiration; vol. 62; 1995; pp. 64-69.

Doyle et al.; "Surfactant Proteins-A and -B are Elevated in Plasma of Patients with Acute Respiratory Failure"; Am J. Respir. Crit. Care Med.; vol. 156; 1997; pp. 1217-1229.

Cleary et al.; "Exudative Lung Injury is Associated with Decreased Levels of Surfactant Proteins in a Rat Model of Meconium Aspiration"; Pediatrics; vol. 100, No. 6; Dec. 1997; pp. 998-1003.

Bernard; "Pneumoproteinaemia: A New Perspective in the Assessment of Lung Disorders"; Eur. Respir. J.; vol. 11; 1998; pp. 801-403.

Japanese Patent Application No. 04009665; Determination of Lung Disease Marker Protein—Using Anti-human Lung Surfactant Apoprotein (SPA Monoclonal Antibody); Abstract only.

Abe et al.; "Clinical Significance of Levels of Lung Surfactant Protein A in Serum, in Various Lung Diseases"; Japanese Journal of Thoracic Diseases; vol. 33, No. 11; Abstract only.

Honda et al.; "Clinical Significance of Serum Surfactant Proteins A and D in Idiopathic Interstitial Pneumonia"; Japanese Journal of Thoracic Diseases 34 Suppl.; vol. 181, No. 5; Abstract only.

Remy-Jardin et al., Martine, "Morphologic Effects of Cigarette Smoking on Airways and Pulmonary Parenchyma in Healthy Adult Volunteers: CT Evaluation and Correlation with Pulmonary Function Tests," Radiology, vol. 186(1):107-115 (1993).

\* cited by examiner

METHOD OF DIAGNOSIS

FIELD OF THE INVENTION

The present invention relates generally to a method of diagnosing or predicting the development of lung damage and more particularly, to a method of diagnosing or predicting the development of alveolo-capillary membrane damage. The method of the present invention is useful inter alia for detecting lung damage or predicting the development of lung damage such as that caused by noxious agents or as an undesirable side effect resulting from exposure to a therapeutic agent and for monitoring the progress of lung damage.

BACKGROUND OF THE INVENTION

The bibliographic details of the publications referred to by author in the specification are collected at the end of the description.

The gas/liquid interface of the lung is lined with a monomolecular layer comprising phospholipid, neutral lipids and specific proteins (surfactant proteins A, B, C and D, herein referred to as SP-A, -B, -C and -D, respectively). Collectively known as "pulmonary surfactant", these compounds lower surface tension, decrease the work of breathing, and stabilise the lung by varying surface tension allowing alveoli of different sizes to co-exist.

Pulmonary surfactant phospholipids are synthesised by Alveolar Type II cells where they are stored in distinctive vesicles known as lamellar bodies. In response to a variety of stimuli, in particular physical distortion of the type II cells, the contents of the lamellar bodies are released into the hypophase, where they hydrate to form a 3-D lattice structure known as tubular myelin. The tubular myelin in turn supplies the monomolecular layer at the gas/liquid interface that possesses the biophysical activity.

The components of the monomolecular layer have a defined life and are constantly replaced. The disaturated phospholipids (DSP) are credited with reducing surface tension to the very low values thought to occur at low lung volumes, while cholesterol, the second most abundant pulmonary surfactant lipid, is thought to affect the rate of adsorption and the fluidity of newly released material. The system is extremely dynamic; in rats, dipalmitoylphosphatidylcholine, the main component of mammalian pulmonary surfactant, has a half-life of ~85 minutes in the alveolus with as much as 85% taken back into type II cells and reutilised (Nicholas et al., 1990).

To date, four proteins, SP-A, -B, -C and -D have been shown to be uniquely associated with mammalian pulmonary surfactant. There is a general consensus that the extremely hydrophobic proteins (SP-B and -C) are functional components of the monomolecular layer, whereas the more hydrophilic protein, SP-A appears to be more involved in pulmonary surfactant homeostasis and host defence, and SP-D is solely involved in host defence.

The adult respiratory distress syndrome (ARDS) represents a severe, diffuse lung injury caused by either direct, via the airways, or indirect, via the blood, trauma. The hallmark of ARDS is a deterioration in blood oxygenation and respiratory system compliance as a consequence of permeability edema. Whereas a variety of different insults may lead to ARDS, a common pathway probably results in the lung damage. Leukocyte activation within the lung, along with the release of oxygen free radicals, arachidonic acid metabolites, and inflammatory mediators such as interleukin-1, proteases, and tumour necrosis factor results in an increase in alveolo-capillary membrane permeability. With the loss of this macromolecular barrier, alveoli are flooded with serum proteins, which impair the function of pulmonary surfactant (Said et al., 1965; Holm et al., 1987). This creates hydrostatic forces that further exacerbates the condition (Jefferies et al., 1988), leading to alveolar edema and a concomitant deterioration in gas exchange and lung compliance.

In the last decade, numerous methods for determining lung permeability have been assessed (Staub et al. 1990). Generally, these have relied upon detecting flux of radiolabels into, or out of, the lung. However, few have been applied clinically because of logistic problems with suitable scanners, stability, and specificity of the labels, and uncertainty over mathematical modelling (Staub et al. 1990). Further, lung damage, such as that induced by a noxious agent, has only been clinically detectable when sufficient damage has occurred for there to be changes in airway resistance or gas exchange. It is well accepted that this reflects relatively advanced lung disease.

Surfactant proteins are normally only found in appreciable amounts in the lung. In the airspaces, SP-A predominantly forms high molecular weight oligomers (~650 kDa) with Stokes radii of ~35 nm (Voss et al., 1988). Although mature SP-B, which associates as a low $M_r$ (~18 kDa) thiol dependent homo-dimer (Johansson et al., 1991), is normally intimately associated with complexes of surfactant phospholipid, (Longo et al., 1992), in vitro and in vivo studies in isolated type II cells suggest that at least some of the protein is secreted into the alveolus as hydrophilic, monomeric proprotein and processing intermediate with $M_r$ of ~45 kDa and ~25 kDa, respectively (Weaver and Whitsett, 1989; Doyle et al., 1997).

In work leading up to the present invention, the inventors have unexpectedly found that serum pulmonary surfactant levels provide an extremely sensitive diagnostic marker of either lung damage, and in particular early stage lung damage, or a predisposition to the development of lung damage.

SUMMARY OF THE INVENTION

Throughout the specification, unless the context required otherwise, the word "comprise", or variations such as "comprises" or "comprising", will be understood to imply the inclusion of a stated element or integer or group of elements or integers but not the exclusion of any other element or integer or group of elements or integers.

Accordingly, one aspect of the present invention relates to a method of diagnosing lung damage in a mammal, said method comprising screening for the modulation of pulmonary surfactant levels in the body fluid of said mammal.

In another aspect there is provided a method of diagnosing lung damage in a mammal, said method comprising screening for the modulation of one or more of SP-A, -B, -C or -D levels in the blood of said mammal.

Yet another aspect of the present invention relates to a method of diagnosing lung damage in a mammal said method comprising screening for the modulation of SP-B levels in the blood of said mammal.

In yet another aspect of the present invention there is provided a method of diagnosing early stage lung damage in a mammal, said method comprising screening for the modulation of pulmonary surfactant levels in the blood of said mammal.

Still yet another aspect of the present invention a method of detecting early stage lung damage in a mammal, said method comprising screening for the modulation of SP-B levels in the blood of said mammal.

In still another aspect of the present invention there is provided a method of diagnosing early stage alveolo-capillary membrane damage in a mammal, said method comprising screening for an increase in SP-B levels in the blood of said mammal.

A further aspect of the present invention provides a method of monitoring for changes in the extent of lung damage in a mammal said method comprising screening for the modulation of pulmonary surfactant levels in the blood of said mammal.

In another further aspect of the present invention there is provided a method of monitoring for an increase in the extent of alveolo-capillary membrane damage in a mammal said method comprising screening for an increase in SP-B levels in the blood of said mammal.

Yet another further aspect of the present invention provides a method of monitoring for a decrease in the extent of alveolo-capillary membrane damage in a mammal said method comprising screening for a decrease in SP-B levels in the serum of said mammal.

Accordingly, another aspect of the present invention relates to a method of diagnosing lung damage in a mammal, said method comprising screening of the modulation of pulmonary surfactant level ratios in the blood of said mammal.

Yet another aspect of the present invention relates to a method of monitoring for changes in the extent of lung damage in a mammal, said method comprising screening for the modulation of pulmonary surfactant level ratios in the blood of said mammal.

In yet another further aspect of the present invention there is provided a method of determining, in a mammal exposed to a lung injury factor, a predisposition to developing severe lung damage, said method comprising screening for the modulation of pulmonary surfactant levels in the blood of said mammal wherein the levels of said pulmonary surfactant are indicative of a predisposition to developing additional lung damage.

Still yet another further aspect of the present invention provides a method of determining, in a mammal which has developed ALI due to exposure to a lung injury factor, a predisposition to developing ARDS said method comprising screening for the modulation of pulmonary surfactants in the blood of said mammal wherein the levels of said pulmonary surfactant are indicative of a predisposition to developing ARDS.

In still yet another further aspect of the present invention this is provided a method of determining, in a mammal which has developed ALI due to exposure to a lung injury factor, a predisposition to the development of ARDS said method comprising screening for the level of SP-A and/or SP-B in the blood of said mammal wherein the level of said SP-A and/or SP-B is indicative of a predisposition to developing ARDS.

Yet another aspect of the present invention provides a method of determining, in a mammal exposed to a lung injury factor, a predisposition to developing severe lung damage said method comprising screening for the modulation of pulmonary surfactant level ratios in the blood of said mammal wherein said ratios are indicative of a predisposition to developing severe lung damage.

Another aspect of the present invention provides a method of determining, in a mammal exposed to a lung injury factor, a predisposition to developing severe lung damage said method comprising correlating the modulation of pulmonary surfactant levels in the body fluid of said mammal with the measurement result of another lung clinical parameter wherein the result of said correlation is indicative of a predisposition to developing severe lung damage.

In another aspect the present invention provides a method of determining, in a mammal exposed to a lung injury factor, a predisposition to developing severe lung damage said method comprising correlating the modulation of pulmonary surfactant levels in the body fluid of said mammal with the lung injury score wherein the result of said correlation is indicative of a predisposition to developing severe lung damage.

Yet another aspect of the present invention provides a diagnostic kit for assaying serum samples comprising in compartmental form a first compartment adapted to contain an agent for detecting pulmonary surfactant and a second compartment adapted to contain reagents useful for facilitating the detection by the agent in the first compartment. Further compartments may also be included, for example, to receive a biological sample. The agent may be an antibody or other suitable detecting molecule.

DETAILED DESCRIPTION OF THE PREFERRED EMBODIMENTS

The present invention is predicated, in part on the identification of a correlation between serum pulmonary surfactant levels and diagnosis of the development or predisposition to the development of lung damage.

Accordingly, one aspect of the present invention relates to a method of diagnosing lung damage in a mammal, said method comprising screening for the modulation of pulmonary surfactant levels in the body fluid of said mammal.

Reference to "body fluid" should be understood to include reference to fluids derived from the body of said mammal such as, but not limited to, blood (including all blood derived components, for example, serum and plasma), urine, tears, bronchial secretions or mucus and fluids which have been introduced into the body of said mammal and subsequently removed such as, for example, the saline solution extracted from the lung following lung lavage. Preferably, the body fluid is blood or urine and even more preferably blood. Reference hereinafter to blood should be read as including reference to all other body fluids.

The term "mammal" as used herein includes humans, primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). Preferably, the mammal is a human or a laboratory test animal. Even more preferably, the mammal is a human. The term "lung damage" encompasses, but is not limited to, lung damage due to, for example, a congenital abnormality or an acquired abnormality such as that due to the on-set of an autoimmune condition, post-transplant lung rejection, infections resulting in an inflammatory response, changes in pressure/volume relationships in the lung, exposure of said mammal to a foreign agent (for example cigarette smoke or dust), a noxious or toxic agent (for example solvents or fumes) or is an undesirable side effect resulting from exposure to a therapeutic agent. Examples of lung damage include, but are not limited to, morphological/structural damage and/or damage to the functioning of the lung such as, for example, accumulation of proteins (for example surfactant) or fluids due to pulmonary clearance impairment or damage to the pulmonary gaseous exchange mechanisms. In a particular embodiment of the present invention said lung damage is alveolo-capillary membrane damage.

Reference herein to "pulmonary surfactant" should be read as including reference to all forms of pulmonary surfactant and derivatives thereof including but not limited to pulmonary phospholipid, pulmonary neutral lipids and pulmonary surfactant proteins, and includes all subunit molecules including, by way of example, the precursor, preproproteins, proprotein and intermediate forms of SP-B. Examples of pulmonary surfactant proteins include SP-A, -B, -C and -D. Preferably, said pulmonary surfactant is SP-A, -B, -C or -D. Reference herein to "SP-A" "SP-B", "SP-C" and "SP-D" should be understood to include reference to all forms of these molecules including all precursor, proprotein and intermediate forms thereof.

Accordingly, there is provided a method of diagnosing lung damage in a mammal, said method comprising screening for the modulation of one or more of SP-A, -B, -C or -D levels in the blood of said mammal.

Levels of circulating SP-A and SP-B depend not only on the relative sizes of the proteins and lung permeability but also the form available to breach the membrane barriers. SP-A binds phospholipid avidly to the extent that there is little of it free in alveoli fluid. In contrast, the predominant form of alveolar immunoreactive SP-B, proprotein and processing intermediate are not bound to surface lipids, possibly allowing freer entry into circulation. Further, that the plasma SP-B/SP-A ratio varies with lung function suggests that plasma SP-B is a more dynamic marker of changes in lung permeability than is SP-A.

In a most preferred embodiment, the present invention relates to a method of diagnosing lung damage in a mammal said method comprising screening for the modulation of SP-B levels in the blood of said mammal.

In a particular aspect, said lung damage may be alveolo-capillary membrane damage.

"Derivatives" of said surfactants includes fragments, parts, portions, mutants and analogs thereof. Derivatives may be derived from insertion, deletion or substitution of an amino acid. Amino acid insertional derivatives include amino and/or carboxyl terminal fusions as well as intrasequence insertions of single or multiple amino acids. Insertional amino acid sequence variants are those in which one or more amino acid residues are introduced into a site in the protein. Deletional variants are characterised by the removal of one or more amino acids from the sequence. Substitutional amino acid variants are those in which at least one residue in the sequence has been removed and a different residue inserted in its place.

The method of the present invention is particularly useful in detecting early stage lung damage. "Early stage" is defined as the period during which the onset and development of lung damage is undetectable or else cannot be confirmed without the aid of one or more invasive procedures. For example, the method of this invention has application in detecting early changes in lung permeability in smokers. "Early stage" should also be understood to include low levels of lung damage such as for example, mild but chronic lung damage. Early changes in lung permeability which may be associated with neutrophil recruitment and initial destruction of lung connective tissue by elastase and reactive oxygen species may be marked by an increase in plasma SP-B levels despite the absence outwardly of any visible symptoms of lung damage.

Accordingly, there is provided a method of diagnosing early stage lung damage in a mammal, said method comprising screening for the modulation of pulmonary surfactant levels in the blood of said mammal.

Preferably said pulmonary surfactant is SP-A, -B, -C or -D and even more preferably SP-B.

In a most preferred embodiment there is provided a method of detecting early stage lung damage in a mammal, said method comprising screening for the modulation of SP-B levels in the blood of said mammal.

In particular, said lung damage may be alveolo-capillary membrane damage.

Although not intending to limit the invention to any one theory or mode of action, alveolo-capillary membrane damage causes an increase in alveolo-capillary permeability. Although immunoreactive SP-A and SP-B are not normally present in appreciable amounts in the systemic circulation, it is thought that the appearance of additional pulmonary surfactant proteins in the serum of patients with lung damage occurs as the result of changes in alveolo-capillary permeability.

Accordingly, the term "modulation" refers to increases and decreases in serum pulmonary surfactant levels relative either to a normal reference level (or normal reference level range) or to an earlier surfactant level result determined from the body fluid of said mammal. A normal reference level is the surfactant level from the body fluid of a mammal or group of mammals which do not have any lung injury. Said reference level may be a discrete figure or may be a range of figures. Said reference level may vary between individual classes of surfactant molecules. For example, the normal level of SP-A may differ to the normal level of SP-B or a particular SP-B subunit. Preferably, said modulation is an increase in blood pulmonary surfactant levels.

According to this preferred embodiment there is provided a method of diagnosing lung damage in a mammal said method comprising screening for an increase in pulmonary surfactant levels in the blood of said mammal.

Preferably, said pulmonary surfactant is SP-A, -B, -C or -D and even more preferably SP-B.

In particular, the lung damage may be early stage lung damage and most particularly alveolo-capillary membrane damage.

According to this most preferred embodiment, there is provided a method of diagnosing early stage alveolo-capillary membrane damage in a mammal, said method comprising screening for an increase in SP-B levels in the blood of said mammal.

Although the preferred method is to detect an increase in blood pulmonary surfactant levels, the detection of a decrease in said surfactant levels may be desired under certain circumstances. For example, to monitor improvement in alveolo-capillary membrane morphology during the course of therapeutic treatment of patients presenting with alveolo-capillary membrane damage or to monitor lung maturation in preterm infants with respiratory distress syndrome.

Accordingly, another aspect of the present invention provides a method of monitoring for changes in the extent of lung damage in a mammal said method comprising screening for the modulation of pulmonary surfactant levels in the blood of said mammal.

Preferably, said pulmonary surfactant is SP-A, -B, -C or -D and even more preferably SP-B.

In particular, the lung damage may be alveolo-capillary membrane damage.

In a most preferred embodiment there is provided a method of monitoring for an increase in the extent of alveolo-capillary membrane damage in a mammal said method comprising screening for an increase in SP-B levels in the blood of said mammal.

In yet another most preferred embodiment there is provided a method of monitoring for a decrease in the extent of alveolo-capillary membrane damage in a mammal said method comprising screening for a decrease in SP-B levels in the serum of said mammal.

The pulmonary surfactant levels utilised in the method of the present invention, in addition to the analysis of absolute values relative to a normal reference level, may also be analysed relative to one another. For example, lung injury results in a differential change in blood SP-A and SP-B levels such that the ratio of SP-B:SP-A is inversely related to lung functions. These ratios may also be compared to normal reference level ratios.

Accordingly, another aspect of the present invention relates to a method of diagnosing lung damage in a mammal, said method comprising screening of the modulation of pulmonary surfactant level ratios in the blood of said mammal.

Reference to "pulmonary surfactant level ratios" should be understood as the ratio of the level of any two or more pulmonary surfactants in a mammal. "Pulmonary surfactant" has the same meaning as hereinbefore defined. The ratio, in a mammal, of one pulmonary surfactant level to another pulmonary surfactant level may be indicative of lung damage.

Preferably, said pulmonary surfactant level ratio is a ratio of the SP-B:SP-A levels and more preferably SP-B preproprotein:SP-A.

Even more preferably said modulation is an increase in the ratio.

Still more preferably, said increase in SP-B:SP-A or SP-B preproprotein:SP-A ratio is indicative of alveolo-capillary membrane damage.

Yet another aspect of the present invention relates to a method of monitoring for changes in the extent of lung damage in a mammal, said method comprising screening for the modulation of pulmonary surfactant level ratios in the blood of said mammal.

The method of the present invention has widespread applications, including but not limited to, as a non-invasive clinical or diagnostic monitor of lung function or morphological/structural damage (such as the onset of alveolo-capillary membrane damage or protein retention) due to, for example, an inflammatory response, exposure to a foreign agent, noxious agent, toxic agent, a side effect of an exposure to a therapeutic agent, post-transplant lung rejection, onset of autoimmunity, pulmonary clearance experiment or gaseous exchange impairment and the onset of alveolo-capillary membrane damage of individuals exposed to foreign agent or a noxious or toxic agent such as individuals who smoke or individuals who are involved in occupations such as welding, spray painting, fibreglass manufacture or involving exposure to passive smoking, which may potentially result in lung damage. The method of the present invention also has application in assessment of the lung health status of any individual irrespective of any perceived predisposition or possibility of having acquired a degree of lung damage.

The method of the present invention extends to diagnosing the degree of lung damage in a mammal based upon an analysis of quantitated pulmonary surfactant levels in the blood of said mammal. For example, the degree of increase in blood pulmonary surfactant level is used as an indicator of the degree of lung damage which the mammal has developed.

Acute lung injury (referred to herein as "ALI") may develop following exposure to a number of factors such as, but not limited to, aspiration of gastric contents, pneumonia, sepsis, massive transfusion, multiple trauma and pancreatitis. A smaller number of patients develop more severe lung injury, sometimes referred to as acute or adult respiratory distress syndrome (referred to herein as "ARDS"), which is a more severe form of ALI with a mortality rate of around 50-60%. Prediction of patients who are at high likelihood of developing ARDS would allow, for example, targeting of novel therapies, and use of complex ventilatory strategies, the cost of which might not otherwise be justified.

Accordingly, another aspect of the present invention provides a method of determining, in a mammal exposed to a lung injury factor, a predisposition to developing severe lung damage, said method comprising screening for the modulation of pulmonary surfactant levels in the blood of said mammal wherein the levels of said pulmonary surfactants are indicative of a predisposition to developing additional lung damage.

The phrase "lung injury factor" should be understood as a reference to any factor which may directly or indirectly cause new lung damage or exacerbate existing lung damage. Examples of said factor include, but are not limited to, mechanical ventilation, hyperoxia, aspiration of gastric contents, pneumonia, sepsis, massive transfusion, multiple trauma and pancreatitis. Lung damage caused by exposure of a mammal to a lung injury factor may or may not be clinically apparent.

The method of the present invention is useful for predicting either those patients, who have been exposed to a lung injury factor, who are likely to develop severe lung injury (and not merely ALI) or those patients, who have developed ALI as a result of exposure to a lung injury factor, who are likely to go on to develop severe lung damage. Accordingly, the phrase "severe lung damage" should be understood in its broadest sense and includes reference to either the development of new lung damage or exacerbation of existing lung damage, such as an increase in its severity. In a particularly preferred embodiment, said mammal has developed ALI due to exposure to a lung injury factor and said severe lung damage is ARDS. Said ALI may or may not be clinically apparent.

According to this preferred embodiment, the present invention provides a method of determining, in a mammal which has developed ALI due to exposure to a lung injury factor, a predisposition to developing ARDS said method comprising screening for the modulation of pulmonary surfactants in the blood of said mammal wherein the levels of said pulmonary surfactant are indicative of a predisposition to developing ARDS.

Most preferably said surfactant is SP-A and/or SP-B.

According to this most preferred embodiment, the present invention provides a method of determining, in a mammal which has developed ALI due to exposure to a lung injury factor, a predisposition to the development of ARDS said method comprising screening for the level of SP-A and/or SP-B in the blood of said mammal wherein the level of said SP-A and/or SP-B is indicative of a predisposition to developing ARDS.

Yet another aspect of the present invention provides a method of determining, in a mammal exposed to a lung injury factor, a predisposition to developing severe lung damage said method comprising screening for the modulation of pulmonary surfactant level ratios in the blood of said mammal wherein said ratios are indicative of a predisposition to developing severe lung damage.

Without limiting the present invention to any one theory or mode of action, SP-A and SP-B are thought to be surrogate markers for disease severity that may not be detected clinically. Accordingly, reference to screening for a "predisposition" to additional lung damage should be understood in its broadest sense to include both screening for those mammals likely to develop additional lung damage and screening for those mammals who have already developed said additional lung damage but are not yet exhibiting clinical symptomology.

In another aspect of the present invention, the predisposition to developing severe lung damage, such as ARDS, can be determined by correlating the measurement results of multiple factors or clinical parameters of lung function or morphology (referred to herein as "lung clinical parameters"), such as the lung injury score, with surfactant levels. For example, the risk of developing ARDS may be determined utilising a model which correlates SP-A and SP-B levels. In a particular embodiment said method correlates SP-A, SP-B and the lung injury score where P=0.012 and $R^2$=46%. The lung injury score is based upon clinical parameters and is used to summarise clinical severity of illness. Although the lung injury score in isolation may not be predictive of the development of ARDS, it is useful when combined with the surfactant level predictive index.

Accordingly, another aspect of the present invention provides a method of determining, in a mammal exposed to a lung injury factor, a predisposition to developing severe lung damage said method comprising correlating the modulation of pulmonary surfactant levels in the blood of said mammal with the measurement result of another lung clinical parameter wherein the result of said correlation is indicative of a predisposition to developing severe lung damage.

Preferably, the present invention provides a method of determining, in a mammal exposed to a lung injury factor, a predisposition to developing severe lung damage said method comprising correlating the modulation of pulmonary surfactant levels in the blood of said mammal with the lung injury score wherein the result of said correlation is indicative of a predisposition to developing severe lung damage.

Preferably said mammal has ALI resulting from exposure to a lung injury factor and said severe lung damage is ARDS.

Even more preferably said surfactants are SP-A and/or SP-B.

It should be understood that although this aspect of the present invention is exemplified with respect to lung injury score, it is not intended to be limited to an assessment of the lung injury score together with the pulmonary surfactant level. Rather, it should be understood to extend to the correlation of any lung clinical parameter, of which lung injury score is merely an example, together with pulmonary surfactant level.

Screening of pulmonary surfactant levels in serum of a mammal can be achieved via a number of techniques such as functional tests, enzymatic tests or immunological tests. Functional tests may include detecting SP-A or -B by their ability to affect release or re-uptake of surfactant or by detecting host defence properties. SP-C may be detected by measuring associated palmitates. Immunological tests may include contacting a serum sample with an antibody specific for a pulmonary surfactant (or group of pulmonary surfactants) or its derivatives thereof for a time and under conditions sufficient for an antibody-pulmonary surfactant complex to form, and then detecting said complex.

In one particular preferred method the target surfactant molecules in the serum sample are exposed to a specific antibody which may or may not be labelled with a reporter molecule. Depending on the amount of target and the strength of the reporter molecule signal, a bound target may be detectable by direct labelling with an antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

The method of the present invention should be understood to include both one off measurements of surfactant levels in a mammal and multiple measurements conducted over a period of time (for example as may be required for the ongoing monitoring of an individual mammal's lung damage status).

Another aspect of the present invention provides a diagnostic kit for assaying serum samples comprising in compartmental form a first compartment adapted to contain an agent for detecting pulmonary surfactant and a second compartment adapted to contain reagents useful for facilitating the detection by the agent in the first compartment. Further compartments may also be included, for example, to receive a biological sample. The agent may be an antibody or other suitable detecting molecule.

Further features of the present invention are more fully described in the following Examples. It is to be understood, however, that this detailed description is included solely for the purposes of exemplifying the present invention. It should not be understood in any way as a restriction on the broad description of the invention as set out above.

Reference to SP-A and SP-B in the following examples should be understood as a reference to immuno-reactive SP-A and SP-B.

Example 1

Sample Preparation and Storage

Blood, was immediately centrifuged in tubes (Disposable Products, Sydney, Australia) containing lithium heparin (plasma) or clot retraction accelerator (serum) at 5,000 rpm for min at room temperature (Megafuge; Heraeus-Christ, Osterode, Germany). Samples stored at −20° C. for batch analysis.

Example 2

Primary Antibody Preparation

SP-A and SP-B were purified from the lavage fluid of patients with alveolar proteinosis. Each protein was emulsified with Freund's complete adjuvant (Difco Laboratories, Detroit, Mich.) and injected subcutaneously into 3 New Zealand white rabbits. The immunizations were boosted with SP-A or SP-B emulsified in Freund's incomplete adjuvant (Difco Laboratories). The rabbits were exsanguinated and IgG precipitated from the serum using 50% (vol/vol) saturated ammonium sulfate. The IgG was reconstituted to the original serum volume in 136.8 mM sodium chloride, 8.1 mM disodium hydrogen phosphate, 2.6 mM potassium chloride, 0.7 mM potassium dihydrogen phosphate containing 0.02% sodium azide and 0.05% (vol/vol) Tween 20 (PBST) and immunoadsorbed overnight at 4° C. against 200 ml of cross-linked, normal human serum. In order to remove any specificalities against soluble blood group A antigenic determinants, the cross-linked serum was prepared from pooled blood comprising equal portions of plasma from five subjects with blood groupings: A (+ve), A (−ve), AB (+ve), O (+ve) and O (−ve). Non-adsorbed components were isolated following centrifugation at 4° C. at 8,000×g (max) for 1 h and the immunoadsorption procedure repeated using fresh human serum immunoadsorbent. Finally, the antibodies were filtered through a 0.2 μm Acrodysc filter (Sterile Acrodysc; Gelman Sciences; Ann Arbor, Mich.; #4192).

Both antibodies react strongly with their antigens in both their native and reduced states. The antibody against SP-B also reacts with its processing intermediate and its proprotein in addition to the mature peptide.

Example 3

ELISA

SP-A and -B were determined by ELISA inhibition assays using SP-A and SP-B purified from alveolar proteinosis lavage fluid as standard.

Samples were assayed in a blind randomized manner. In order to free the SP-A and -B from any associated plasma or surfactant components, all samples were treated in the following manner. 125 μl aliquots were diluted in 500 μl of 10 mM Tris, 1 mM EDTA containing 0.25% BSA (pH 7.4). After vortexing at room temperature for 10 min, 125 μl of solution containing 3% SDS and 12% Triton X-100 (v/v) was added to each sample. The samples were again vortexed for 10 min and surfactant protein concentration determined using an ELISA inhibition assay.

The SP-A and SP-B assays were performed in 2 parts. Costar ELISA plates (Costar, Cambridge, Mass.; #2595) were coated overnight at 4° C. with purified SP-A or -B (1 μg/ml) in a solution containing 15 mM sodium carbonate, 35 mM sodium bicarbonate and 0.02% sodium azide (pH 9.6). The coated plates were washed with PBST prior to use.

In a separate ELISA plate dilutions of the samples and standards (which were routinely included in each plate) were incubated with aliquots of the respective primary antibody. Each treated sample was assayed at four 2-fold dilutions in PBST containing 0.25% BSA (PBST/BSA). Standard curves comprising eight 2-fold serial dilutions in PBST/BSA (SP-A: 1.95 ng/ml to 250 ng/ml; SP-B: 7.8 ng/ml to 1.0 μg/ml) were constructed. Samples were assayed in duplicate while standards were assayed in quadruplicate.

After 90 min aliquots were transferred to the plates coated with SP-A and SP-B and incubated at room temperature for an additional 90 min. These plates were then washed with PBST and incubated at room temperature for 90 min with aliquots of alkaline phosphatase-conjugated sheep anti-rabbit polyclonal IgG (Silenus Laboratories) diluted in PBST/BSA. After washing with PBST the plates were developed at room temperature with 15 mM disodium p-nitrophenyl phosphate (Sigma 104 phosphatase substrate tablets; Sigma Chemical Co; St Louis, Mo.) in 1.0 M diethanolamine and 0.5 mM magnesium chloride. At ~1 h the absorbance of the substrate was measured at 405 nm using a Dynatech MR5000 reader (Dynatech Laboratories, Chantilly, Va.). An AssayZap program (Biosoft, Ferguson, Mo.) was used to generate a standard curve and to compute the concentration of the surfactant protein in each sample based on their immunoreactivity.

Statistics

Results are expressed as mean±SE. Non-parametric analyses were used since we have no reason to assume that the data is normally distributed. The Mann-Whitney U Test or the Wilcoxon Matched Pairs Sign Rank Test was used for all comparisons.

Example 4

Normal Plasma Surfactant Protein Levels and Smoking

Cigarette smoking has been implicated as a factor causing lung damage. This includes damage to the airway and the lung parenchyma, and may manifest as a broad range of conditions including bronchitis, emphysema and some lung cancers. However, many smoking subjects have no clinically evident lung damage and are asymptomatic. Consequently a 'normal plasma surfactant protein level' may need to be described for non-smokers and smokers with the 'normal smoking level' describing asymptomatic lung damage.

Since cigarette smoking may acutely and reversibly increase lung epithelial permeability through smoke mediated release of vasoactive neuropeptides (tachykinins) from sensory nerves in the airways (Germonpre et al, 1995; Geppetti et al, 1993; Lei et al, 1993; Nadel & Borson, 1991), smokers are requested to refrain from smoking for at least 4 h prior to screening. Two ml of peripheral blood is drawn from an antecubital vein and centrifuged in lithium heparin tubes at 5,000 rpm for 5 min at room temperature (Megafuge; Heracus-Christ; Osterode, Germany) immediately following collection.

Blood was sampled from 66 asymptomatic adults not known to have any lung disease. The subjects age, sex and smoking history were noted. The results are shown in Table 1.

TABLE 1

|  | Non-smokers | Smokers | P-value |
|---|---|---|---|
| Age (years) | 30.4 ± 1.7 | 33.7 ± 1.3 | NS |
| Sex (M/F) | 16/19 | 16/15 | NS |
| SP-A (ng/ml) | 248.4 ± 14.1 | 242.3 ± 29.8 | NS |
| SP-B (ng/ml) | 2026.9 ± 91.8 | 3046.2 ± 209.1 | <0.001 |

(means ± SE, Mann-Whitney U-test)

Thirty one subjects had smoked 20.1±2.7 pack/years of cigarettes, and this correlated with their SP-B levels with an $R^2$ of 33% and a P-value=0.0005. The 95% confidence intervals from these data for SP-A were 219.7-277.1 (ng/ml) for non-smokers and 181.4-303.2 (ng/ml) for smokers, and for SP-B 1840-2213 (ng/ml) for non-smokers and 2619-3473 (ng/ml) for smokers.

The plasma SP-B level is elevated in asymptomatic smokers compared to asymptomatic non-smokers, consistent with impaired lung health in smokers. This supports the claim that the plasma SP-B level is an extremely sensitive marker of lung health. The 95% confidence intervals may be used to estimate a plasma level of each surfactant protein that is elevated, indicating lung damage, for that cohort. Subsequent data may refer to elevated levels in comparison with this data or an elevation from the baseline plasma level from longitudinal studies in an individual subject.

Example 5

Exercise-Induced Impairment of the Alveolocapillary Barrier in Humans

Eighteen male subjects (mean±SE, age: 18 to 29 yr, 24.3±0.80 yr; height: 162 to 188 cm, 178.6±1.72 cm; weight: 53 to 95 kg, 75.9±2.61 kg), all nonsmokers, arrived in the pulmonary function laboratory between 7.00 and 8.00 am, after fasting from midnight.

Single peripheral blood samples were drawn from an antecubital vein from half of the subjects. The remaining nine subjects were subjected to an exercise regimen and blood sampled immediately afterwards. One week later the subject groups were reversed. The procedure was repeated on 13 of the subjects ~8 wk later.

Acute Exercise Procedure

Subjects were equipped with an ear pulse oximeter (Criticare 504-USP, CSI-USA, Waukesha, Wis.) for monitoring heart rate. The subjects cycled at 60 rpm (Ergometry System Model 380B; Siemens-Elema AB, Sona, Sweden) and the load was increased to bring heart rate to approximately 90% of the theoretical maximal heart rate, calculated as 210-(0.6× age), within 10 min. Cycling continued for a further 20 min, and the load was continuously adjusted so as to maintain heart rate as close as possible to this value. In all cases this involved the gradual reduction of load over the period.

Results

Serum SP-B levels are significantly (<0.01, n=31; Wilcoxon Matched-Pairs Signed-Rank test) elevated after exercise (rest: 1656.5 ng/ml±94.46; exercise; 1899.8 ng/ml±128.35; mean±SE).

In humans pulmonary capillary pressure may peak at 35 mmHg during strenuous exercise and this is sufficient to impair the integrity of the blood-gas barrier. Those findings are consistent with this and illustrate that a rapid rise in pulmonary capillary pressure may produce stress failure in the pulmonary capillaries and increase alveolo-capillary permeability.

By way of contrast, horses have comparatively a far greater cardiac output, furthermore, thoroughbreds are selectively bred to maximize performance. Consequently, pulmonary capillary pressure may reach 200 mmHg at the base of their lungs during strenuous exercise. Although the blood-gas barrier of horses is more resistant to stress failure than that of many other mammals, faced with these pressures it is hardly surprising that ~90% of 5 yr old thoroughbreds have suffered at least one episode of gross pulmonary haemorrhage, with an appreciable cost to the racing industry. Circulating SP-A & -B are sensitive markers of hydrostatic pressure-induced lung damage.

Since during strenuous exercise, pulmonary vascular pressures are elevated and result in increased lung water and increased alveolo-capillary permeability in race horses, this results in rupture of pulmonary blood vessels which manifest as blood in the alveolos. Blood or blood product surfactant protein levels are monitored during the training, racing and during recovery from exercise induced lung damage.

Example 6

Acute Respiratory Failure

Acute respiratory failure may be due to multiple causes such as cardiac pulmonary edema, polytrauma, multiple transfusion, sepsis or serious infection, aspiration of gastric contents, pneumonia, disseminated intravascular coagulation and pancreatitis.

Blood was sampled from 83 patients in the Critical Care Unit at Flinders Medical Centre, the plasma isolated and stored at −20° C. prior to analysis. Their age, sex, and lung injury score (LIS)[1] derived from a chest radiograph score, the partial pressure of oxygen to inspired oxygen ratio ($PaO_2/FiO_2$ ratio), the amount of positive end-expiratory pressure and the respiratory system compliance was calculated. Ten subjects were mechanically ventilated for reasons other than respiratory failure, and were thought to have normal lung function. The remaining 73 patients had acute respiratory failure and are subdivided depending upon the underlying cause.

Results

TABLE 2

| (means ± SE) | | | | | |
|---|---|---|---|---|---|
|  | Number | Male/Female | Age | Lung Injury Score | Plasma SP-A (ng/ml) | Plasma SP-B (ng/ml) |
| Ventilated controls | 10 | 7/3 | 36 ± 8 | 0.3 ± 0.2 | 227 ± 30 | 1998 ± 169 |
| Cardiac pulmonary edema | 10 | 7/3 | 36 ± 8 | 0.3 ± 0.2 | 268 ± 22 | 3646 ± 635 |
| Polytrauma | 4 | 4/0 | 33 ± 4 | 1.3 ± 0.2 | 444 ± 108 | 4174 ± 1197 |
| Multiple transfusion | 9 | 8/1 | 70 ± 3 | 2.1 ± 0.2 | 368 ± 41 | 3456 ± 384 |

TABLE 2-continued (means ± SE)

|  | Number | Male/Female | Age | Lung Injury Score | Plasma SP-A (ng/ml) | Plasma SP-B (ng/ml) |
|---|---|---|---|---|---|---|
| Sepsis | 14 | 9/5 | 65 ± 3 | 2.3 ± 0.3 | 467 ± 233 | 4373 ± 819 |
| Aspiration | 13 | 9/4 | 70 ± 3 | 2.3 ± 0.1 | 500 ± 67 | 8110 ± 1338 |
| Pneumonia | 12 | 8/4 | 58 ± 5 | 2.2 ± 0.3 | 528 ± 86 | 9725 ± 1735 |
| Disseminated intravascular coagulation | 2 | 1/1 | 36 ± 18 | 2.5 ± 0.5 | 452 ± 232 | 6099 ± 4312 |
| Pancreatitis | 6 | 4/2 | 49 ± 4 | 2.1 ± 0.2 | 414 ± 119 | 4768 ± 1696 |
| Liver failure | 3 | 1/2 | 31 ± 6 | 3.4 ± 0.3 | 531 ± 106 | 7407 ± 2627 |

The ventilated control subjects had normal plasma SP-A and SP-B levels (Table 2). However, there are elevated plasma levels in a wide variety of causes of acute respiratory failure. The highest SP-A and SP-B levels were generally found in patients with acute respirator failure due to aspiration pneumonia or pneumonia, both direct causes of lung injury. The lowest, but still elevated levels of SP-A and SP-B were found in patients with cardiac pulmonary edema. This is consistent with elevated plasma levels of these proteins representing an increase in alveolo-capillary permeability, and that this elevation is generally greatest in direct causes of lung injury and a lesser elevation in lung injury due to an elevation in pulmonary hydrostatic pressure, that is an indirect cause of lung injury.

Example 7

Monitoring of Therapeutic, Lung Toxic Drugs—for Example Methotrexate

Methotrexate is a commonly used immuno suppressive drug for the treatment of a variety of conditions including rheumatoid arthritis. However, a side effect of methotrexate is lung damage which has, to date, been detected by symptoms such as changes in blood gases or sophisticated lung function tests. Said methods only detect advanced lung damage. Blood or blood product surfactant protein levels are used to monitor the safety of methotrexate therapy by detecting any increase in alveolo-capillary permeability. Monitoring comprises a preliminary test followed by intermittent (daily, weekly or monthly) testing.

Example 8

Monitoring of Bleomycin Treated Patients

Bleomycin in an anti-cancer or cytotoxic drug known to cause pulmonary toxicity. Risk factors for bleomycin-induced lung injury include increasing dose, concurrent use of other cytotoxic drugs, radiotherapy and supplemental oxygen. Three main mechanisms are thought to account for lung injury. Direct cytotoxicity from reactive oxygen species causes a permeability pulmonary edema, similar to acute lung injury (ALI). Lung injury may also occur due to hypersensitivity or idiosyncratic reactions. None of the other cytotoxic drugs alone and used in the doses given to the patients described commonly cause pulmonary toxicity.

Listed in Table 3 are four patients who were treated with bleomycin and other cytotoxic drugs. None of the patients had any respiratory symptoms, none had known lung involvement with cancer and all were non-smokers. Blood was sampled at rest and the plasma frozen at −20° C. until assayed.

TABLE 3

Chemotherapy data

| Diagnosis | Age | Sex | Smoking history | PFT's[1] | Bleomycin dose (units) | Other cytotoxics | SP-A (ng/ml) | SP-B (ng/ml) |
|---|---|---|---|---|---|---|---|---|
| Testicular cancer[2] | 39 | M | ceased 15 years |  | 60 | cisplatin 450 mg etoposide 2.2 g | 360.2 | 1547.9 |
| Hodgkin's lymphoma[3] | 23 | M | never | normal | 90 | doxorubicin 450 mg vinblastine 110 mg dacarbazine 6.8 g | 174.3 | 1730.0 |
| Non-Hodgkin's lymphoma | 74 | M | never |  | 15 | cyclophosphamide 1 g etoposide 100 mg procarbazine 100 mg prednisolone 75 mg | 265.5 | 2598.2 |
| Non-Hodgkin's lymphoma | 60 | F | never |  | 30 | cyclophosphamide 2.2 g etoposide 390 mg procarbazine 1 g prednisolone 1 g | 413.6 | 1382.6 |

[1]Pulmonary function tests include lung volumes, transfer factor and bronchodilator responses were normal prior to starting cytotoxic chemotherapy.
[2]A week later a further 30 units of bleomycin his SP-A and SP-B levels were still elevated but had fallen to 295.5 and 1199.8 ng/ml respectively.
[3]Two weeks after a further cycle of chemotherapy which included a further 18 units of bleomycin his SP-A level had risen to 339.9 ng/ml and his SP-B had risen to 5512.8 ng/ml.

Results
    The plasma SP-B level in patient 3 is elevated, but the SP-B levels in the other patients are normal. This is consistent with individual variability to the lung toxic effects of bleomycin.
    Patient 2: The elevation of SP-A and SP-B with a further dose of bleomycin (see footnote 3) is consistent bleomycin-induced lung damage leading to an increase in alveolo-capillary permeability and an increase in the plasma surfactant protein levels. This indicates that surfactant protein levels may be used to monitor the administration of lung toxic drugs.

Patient 1: The fall in SP-A and SP-B after further chemotherapy is consistent with repair and resolution of bleomycin-induced lung damage. This indicates that surfactant protein levels may be used to monitor resolution of lung damage due to a toxic drug.

Example 9

Radiotherapy Induced Lung Damage

Radiation therapy which either targets or inadvertently exposes the lung may result in lung damage. While this is often relatively asymptomatic, some patients become symptomatic and may develop respiratory failure. This occurs in the weeks following initiation of treatment. Surfactant protein levels are used to monitor this lung damage allowing individualisation of radiotherapy dose and/or frequency.

Case 1: Blood was sampled from a 19 year old non-smoking male 2 weeks after a course of radiotherapy for Hodgkins lymphoma. He had no respiratory symptoms and prior chemotherapy was not thought to be lung toxic. His Case 2: Blood was sampled from a 57 year old woman 3 weeks after radiotherapy for a squamous cell carcinoma of the lung. She had ceased smoking recently and had no change in her respiratory symptoms. Prior chemotherapy was not thought to be lung toxic. Her plasma SP-A was markedly elevated at 963.6 ng/ml and her SP-B was elevated at 2742.2 ng/ml.

Symptoms from radiotherapy induced lung toxicity commonly occur some weeks after treatment. The elevation in surfactant proteins in both patients is consistent with the elevation being due to radiotherapy induced lung damage and an increase in alveolo-capillary permeability. Consequently, surfactant protein levels are used to monitor radiotherapy, to individualise therapy and to monitor rescue treatments such as growth factors.

Example 10

Monitoring Herbicide Induced Lung Damage

Paraquat is a widely used herbicide that destroys the lipid cell membrane through production of oxygen radicals. This is also thought to be the mechanism of toxicity, predominantly pulmonary, in humans. Typically acute lung injury develops some days following ingestion and this usually progresses to fatal respiratory failure due to the development of the acute respiratory distress syndrome with marked pulmonary fibrosis.

Blood was sequentially sampled from a patient following ingestion of paraquat for measurement of circulating surfactant proteins and for documentation of blood oxygenation.

In the FIGURE the initial blood oxygenation to inspired oxygen ratio ($PaO_2/FiO_2$ ratio) is normal and remains unchanged until 64 hours following presentation. The sudden fall in the $PaO_2/FiO_2$ ratio is evidence of lung damage. The plasma SP-B level was also normal at presentation by suddenly increased at 54 hours following ingestion, 10 hours before the change in blood oxygenation.

This data demonstrates that surfactant proteins are early markers of lung damage, and that this precedes clinical diagnosis of lung damage (FIG. 1).

Example 11

Prediction of Severe Lung Damage

Following a predisposing cause patients may develop acute lung injury (ALI) and require respiratory support for acute respiratory failure. When this progresses to more severe lung damage it may be termed acute respiratory distress syndrome (ARDS). Prediction of which patient swill develop ARDS has many therapeutic implications.

43 patients treated in the critical Care Unit and Flinders Medical Centre had blood sampled within 12 hours of developing ALI which was defined as a lung injury score (LIS) <2.5. Their sex, age, LIS and the development of ARDS (LIS>2.5) were documented. Plasma was isolated and frozen at −20 C until assayed. The data is presented as mean±SE, and the data compared with a Mann-Whitney U-test.

Results

TABLE 4

| | Does not develop ARDS | Develops ARDS | P-value |
|---|---|---|---|
| Age | 60 ± 4 | 61 ± 3 | NS |
| Male/Female | 17/7 | 11/8 | NS |
| LIS | 1.7 ± 0.1 | 1.9 ± 0.1 | NS |
| SP-A (ng/ml) | 393 ± 36 | 514 ± 55 | NS |
| SP-B (ng/ml) | 4162 ± 502 | 8222 ± 1319 | 0.017 |

The plasma level of SP-B is significantly higher in subjects with ALI who will develop ARDS than those who do not (Table 4). Since the LIS is no different between the two groups, and there is no difference in age or sex distribution, this cannot be predicted on clinical grounds. This indicates that surfactant protein levels may be used to predict the development of severe lung injury.

Example 12

Surfactant Protein Ratios

The ratio of surfactant components is useful in understanding, diagnosing and monitoring disease processes. As an example Table 5 lists SP-B/A ratios for some of the patient groups studied.

TABLE 5

| | Number | Male/Female | Age | Lung Injury Score | SP-B/A Ratio |
|---|---|---|---|---|---|
| Non-smokers | 35 | 16/19 | 30.4 ± 1.7 | | 8.6 ± 0.5 |
| Smokers | 31 | 16/15 | 33.7 ± 1.3 | | 15.2 ± 1.6 |
| ALI only | 24 | 17/7 | 60 ± 4 | 1.7 ± 0.1 | 11.6 ± 1.2 |
| Pre-ARDS | 19 | 11/8 | 61 ± 3 | 1.9 ± 0.1 | 16.8 ± 2.7 |
| Ventilated controls | 10 | 7/3 | 36 ± 8 | 0.3 ± 0.2 | 9.9 ± 1.1 |
| Cardiac pulmonary edema | 10 | 7/3 | 36 ± 8 | 0.3 ± 0.2 | 13.8 ± 2.2 |
| Polytrauma | 4 | 4/0 | 33 ± 4 | 1.3 ± 0.2 | 9.4 ± 1.6 |
| Multiple transfusion | 9 | 8/1 | 70 ± 3 | 2.1 ± 0.2 | 10.4 ± 1.5 |
| Sepsis | 14 | 9/5 | 65 ± 3 | 2.3 ± 0.3 | 9.9 ± 1.3 |
| Aspiration | 13 | 9/4 | 70 ± 3 | 2.3 ± 0.1 | 17.5 ± 2.6 |
| Pneumonia | 12 | 8/4 | 58 ± 5 | 2.2 ± 0.3 | 21.6 ± 4.0 |
| Disseminated intravascular coagulation | 2 | 1/1 | 36 ± 18 | 2.5 ± 0.5 | 15.9 ± 2.0 |
| Pancreatitis | 6 | 4/2 | 49 ± 4 | 2.1 ± 0.2 | 11.5 ± 1.8 |
| Liver failure | 3 | 1/2 | 31 ± 6 | 3.4 ± 0.3 | 11.8 ± 7.3 |

The SP-B/A ratio for non-smokers is the same as that for ventilated control subjects, however the SP-B/A ratio is higher for smokers. This is consistent with SP-B levels reflecting leakage through smaller pores in the alveolo-capillary membrane. There is also a marked elevation in the SP-B/A ratio in the direct causes of lung damage such as pneumonia and aspiration compared to the indirect causes such as septis. This is consistent with a greater increase in permeability in this group. Consequently the SP-A/B ratio can be used in addition to the absolute surfactant levels.

Example 13

Monitoring Vascular SP-A and SP-B Levels as Surrogate Markers of Pulmonary Surfactant Status Non-pulmonary vascular and extravascular levels of SP-A & -B will depend not only on the alveolo-capillary permeability, but also on the alveolar levels.

Primary alveolar proteinosis is a chronic disease of unknown pathogenesis characterised by the diffuse accumulation of excess surfactant in the airspaces. Patients are usually less than 45 years old with an appreciable proportion adolescents and infants. Although whole-lung lavage has become standard therapy, the clinical course varies markedly. It is thought that surfactant synthesis and secretion in primary alveolar proteinosis patients is normal and that surfactant accumulation in the alveolus arises through an impairment in its clearance. Congenital alveolar proteinosis is also characterised by the diffuse accumulation of excess surfactant in the airspaces. As distinct from primary alveolar proteinosis, there are now a number of established cause for the congenital phenotype. These include, but are not limited to, the lack of expression of the GM-CSF Receptor beta-common chain and molecular defects in the SP-B gene.

Single peripheral blood samples were drawn from an antecubital vein from 12 patients (30 yr±2.7; mean±SE) diagnosed with primary alveolar proteinosis. Patients were diagnosed as idiopathic both clinically and on the basis of either transbronchial or open lung biopsy.

Single peripheral blood samples were also drawn from an antecubital vein from 3 infants (<1 yr) diagnosed with congenital alveolar proteinosis. The infants expressed normal GM-CSF Receptor components and did not have the SP-B defect molecularly or on immunohistochemistry.
Results Serum SP-A and SP-B were greatly elevated in patients with primary or congenital alveolar proteinosis (all groups p<0.001; Mann-Whitney U test) compared to normal. (Table 6).

TABLE 6

|  | Primary Alveolar Proteinosis | Congenital Alveolar Proteinosis |
| --- | --- | --- |
| SP-A | 1440.5 ng/ml ± 259.05 | 3096.2 ± 834.17 |
| SP-B | 17845.2 ng/ml ± 3065.16 | 39928.1 ± 5884.91 |

(mean ± SE

Circulating SP-A and -B are greatly elevated in patients with primary or non-SP-B deficient-congenital alveolar proteinosis. Since alveolo-capillary permeability is normal in these patients this illustrates that circulating SP-A & -B mark changes in pulmonary surfactant levels.

Approximately 30% of primary alveolar proteinosis cases resolve spontaneously, some require multiple lavage over extended periods, while others progress to disseminated lung disease. If left untreated ~30% of patients progress to dyspnea, hypoxemia and death. In the absence of lung transplant, the prognosis for infants with congenital alveolar proteinosis is poor.

Currently, the severity of alveolar proteinosis is only poorly reflected by indirect parameters such as blood oxygenation. Circulating surfactant protein levels offer a direct non-invasive method of monitoring this condition. The test also has particular utility in the diagnosis of congenital forms of the condition where SP-B may, or may not, be present. In addition, circulating surfactant protein levels offer a direct non-invasive method of monitoring surfactant levels and lung maturation in pre-term infants with respiratory distress syndrome.

Example 14

The Monitoring of SP-A and -B Levels in Both Vascular and Extravascular Fluids

Single pleural fluid and matching bloods were collected from 88 patients who had diagnostic of therapeutic thoracentesis (63±14 yr; mean±SE). The study population included patients with neoplasia (metastatic carcinoma, hematologic malignancy, and mesothelioma), inflammatory pleural effusion (parapneumonic, postsurgical, emphysema, subphrenic abscess, collagen vascular disease, as well as other various causes), congestive heart failure, and patients with cirrhosis and hydrothorax.
Results Pleural SP-A and SP-B levels are significantly elevated (both p<0.001, n=88; Wilcoxon Matched-Pairs Signed-Rank test) compared to the matching serum samples (Table 7). Both serum SP-A and -B significantly relate to the pleural levels (SP-A; p<0.001, $r_s$=0.57, n=88; SP-B; p<0.001 $r_s$=0.4).

TABLE 7

| Serum SP-A | 290.5 ng/ml ± 22.36 |
| --- | --- |
| Serum SP-B | 2599.9 ng/ml ± 165.6 |
| Pleural Serum SP-A | 632.9 ng/ml ± 154.91 |
| Pleural Serum SP-B | 4877.8 ng/ml ± 685.76 | mean ± SE

Although the epithelium and endothelium generally restricts the movement of molecules larger than albumin ($M_r$ 67 kD, hydrodynamic radius ~3.5 nm), proteins diffuse down their concentration gradients from the lung alveolar hypophase and between vascular and extravascular compartments. The levels of both vascular, and extravascular, SP-A and -B are sensitive markers of alveolo-capillary permeability and lung health.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Doyle, I. R., Jones, M. E., et al., *Am. J. Respir. Crit. Care. Med.* 149:1619-1627 (1994)

Doyle, I. R., Bersten, A. D. and Nicholas, T. E., *Am. J. Respir. Crit. Care Med.* 156:1217-1219 (1997)

Geppetti, P., Bertrand, C., et al., *Br. J. Pharm.* 108:646-50 (1993)

Germonpre, P. R., Joos, G. F., et al., 329:185-203 (1995)

Holm, B. A., and Notter, R. H., *J. Appl. Physiol.* 63:1434-1442 (1987)

Jefferies, A. L., Kawano, T., Mori, S., and Burger R., *J. Appl. Physiol.* 64:5620-5628 (1988)

Johansson, J., Curstedt, T. and Jornvall, H., *Biochemistry* 30:6917-6921 (1991)

Lei, Y. H., Barnes, P. J. et al., *Eur. J. Pharmacol.* 239:257-9 (1993)

Longo, M. L., Waring, A. and Zasadzinski, A. N., *Biophys. J.* 63:760-773 (1992)

Nadel, J. A. and Borson, D. B. *Am. Rev. Respir. Dis.* 143:S33-36 (1991)

Nicholas, T. E., Bar, H. A., Power, J. H. T. and Jones, M. E. *Amer. J. Physiol.* 259:L238-L246 (1990)

Nicholas, T. E., *NIPS*. 8:12-8 (1993)

Said, S. I., Avery, M. E., Davis, R. K., Banerjee, C. M., EI-Gohary, M., *J. Clin. Invest.* 44:458-464 (1965)

Staub, N. C. and Hyde, R. W. et al. *Am. Rev. Respir. Dis.* 141:1071-1977 (1990)

Voss, T., Eistetter, H., Schafer, K. P. and Engel, J., *J. Mol. Biol.* 201:219-227 (1988)

Weaver, T. E. and Whitsett, J. A., *Am. J. Physiol.* 257:L100-L108 (1989)

Yogalingam, G., Doyle, I. R., et al., *Am. J. Physiol.* 14:L320-L330 (1996)

The invention claimed is:

1. A method of diagnosing lung damage in a mammal, said method comprising:
   identifying a mammal who is asymptomatic to lung damage;
   measuring a level of SP-B in a body fluid of the mammal;
   comparing the measured level of SP-B to a normal reference level of SP-B; and
   detecting an increase in the measured level of SP-B in the mammal, wherein said increase is indicative of lung damage in the mammal.

2. A method of diagnosing lung damage in a mammal who has been exposed to a lung injury factor, said method comprising:
   identifying a mammal who has been exposed to a foreign agent, a noxious or toxic agent, or a therapeutic agent;
   measuring a level of SP-B in a body fluid of the mammal;
   comparing the measured level of SP-B to a normal reference level of SP-B; and
   detecting an increase in the measured level of SP-B in the mammal, wherein said increase is indicative of lung damage in the mammal,
   wherein the clinical diagnosis of lung damage in the mammal cannot otherwise be confirmed without the aid of one or more invasive procedures.

3. The method of claim 1, wherein said body fluid is blood.

4. The method of claim 2, wherein said body fluid is blood.

5. A method of diagnosing alveolo-capillary membrane damage in a mammal, said method comprising:
   identifying a mammal who is asymptomatic to alveolo-capillary membrane damage;
   measuring a level of SP-B in a body fluid of the mammal;
   comparing the measured level of SP-B to a normal reference level of SP-B; and
   detecting an increase in the measured level of SP-B in the mammal, wherein said increase is indicative of alveolo-capillary membrane damage in the mammal.

6. The method of claim 5, wherein the clinical diagnosis of alveolo-capillary membrane damage in the mammal cannot otherwise be confirmed without the aid of one or more invasive procedures.

7. The method of claim 5, wherein said body fluid is blood.

8. The method of claim 6, wherein said body fluid is blood.

9. The method of claim 1, wherein the mammal is a human.

10. The method of claim 5, wherein the mammal is a human.

11. The method of claim 5, wherein said increase is indicative of lung damage in the mammal.

12. The method of claim 2, wherein the mammal has been exposed to smoke, methotrexate, bleomycin, radiation therapy, or paraquat.

13. The method of claim 1, further comprising measuring the SP-B level in the body fluid by:
   using a diagnostic kit for assaying a serum sample, said diagnostic kit comprising an agent for detecting SP-B and a reagent.

14. The method of claim 2, further comprising measuring the SP-B level in the body fluid by:
   using a diagnostic kit for assaying a serum sample, said diagnostic kit comprising an agent for detecting SP-B and a reagent.

15. The method of claim 5, further comprising measuring the SP-B level in the body fluid by:
   using a diagnostic kit for assaying a serum sample, said diagnostic kit comprising an agent for detecting SP-B and a reagent.

* * * * *